United States Patent … US 6,991,628 B2
Vito et al. … Date of Patent: Jan. 31, 2006

(54) DEVICE AND METHOD FOR CREATING A VASCULAR GRAFT IN VITRO

(75) Inventors: Raymond P. Vito, Atlanta, GA (US); Jack C. Griffis, III, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 10/652,775

(22) Filed: Aug. 29, 2003

(65) Prior Publication Data

US 2004/0044268 A1 Mar. 4, 2004

Related U.S. Application Data

(60) Division of application No. 09/994,500, filed on Nov. 27, 2001, now Pat. No. 6,641,576, which is a continuation-in-part of application No. 09/322,095, filed on May 28, 1999, now Pat. No. 6,322,553, said application No. 09/322,095.

(60) Provisional application No. 60/274,702, filed on Mar. 9, 2001, provisional application No. 60/087,027, filed on May 28, 1998.

(51) Int. Cl.
*A61B 17/00* (2006.01)

(52) U.S. Cl. .......................... 606/1; 606/159; 606/194; 600/36; 623/1.1; 623/903; 435/293.1

(58) Field of Classification Search ............... 606/1, 606/159, 194; 600/36; 623/1.1, 903; 128/898; 435/1.2, 395, 400, 401, 284.1, 293.1
See application file for complete search history.

(56) References Cited

U.S. PATENT DOCUMENTS

| | | |
|---|---|---|
| 4,846,181 A | 7/1989 | Miller |
| 4,863,469 A | 9/1989 | VanBeek et al. |
| 4,978,348 A | 12/1990 | Ilizarov |
| 4,990,131 A | 2/1991 | Dardik et al. |
| 5,078,726 A | 1/1992 | Kreamer |
| 5,083,576 A | 1/1992 | Ruiz-Razura et al. |
| 5,344,425 A | 9/1994 | Sawyer |
| 5,376,110 A | 12/1994 | Tu et al. |
| 5,441,540 A | 8/1995 | Kim |
| 5,549,664 A | 8/1996 | Hirata et al. |
| 5,556,428 A | 9/1996 | Shah |
| 5,662,710 A | 9/1997 | Bonutti |
| 5,702,419 A | 12/1997 | Berry et al. |
| 5,713,917 A | 2/1998 | Leonhardt et al. |
| 5,769,893 A | 6/1998 | Shah |
| 5,879,713 A | 3/1999 | Roth et al. |

(Continued)

OTHER PUBLICATIONS

U.S. Appl. No. 09/994,241, filed Nov. 27, 2001, Vito et al.

(Continued)

*Primary Examiner*—Rosiland Rollins
(74) *Attorney, Agent, or Firm*—Sutherland Asbill & Brennan LLP

(57) ABSTRACT

Methods and apparatus are provided for forming a vascular graft in vitro by axially distending a blood vessel to induce growth. The apparatus comprises a chamber containing a tissue culture medium, an inlet cannula, an outlet cannula, and a means for moving the inlet cannula, the outlet cannula, or both, to axially stretch a donor blood vessel secured between the inlet cannula and the outlet cannula in a submerged position in the tissue culture medium, wherein the inlet cannula, the outlet cannula, and the donor blood vessel are secured together to form a conduit through which the tissue culture medium can flow.

22 Claims, 11 Drawing Sheets

U.S. PATENT DOCUMENTS

| | | | |
|---|---|---|---|
| 5,888,720 | A | 3/1999 | Mitrani |
| 5,899,936 | A | 5/1999 | Goldstein |
| 5,902,228 | A | 5/1999 | Schulsinger et al. |
| 6,160,084 | A | 12/2000 | Langer et al. |
| 6,322,553 | B1 | 11/2001 | Vito |
| 2003/0097040 | A1 | 5/2003 | Clerin et al. |

OTHER PUBLICATIONS

Bergsma, et al., "Low Recurrence of Angina Pectoris After Coronary Artery Bypass Graft Surgery With Bilateral Internal Thoracic and Right Gastroepiploic Arteries," *Circulation* 97(24):2402-05 (1998).

Birukov, et al., "Stretch Affects Phenotype and Proliferation of Vascular Smooth Muscle Cells," *Mol Cell Biochem.* 144(2): 131-39 (1995).

Cooley, "Coronary Bypass Grafting With Bilateral Internal Thoracic Arteries and the Right Gastroepiploic Artery," *Circulation* 97(24):2384-85 (1998).

Cohen, et al., "Acute Intraoperative Arterial Lengthening for Closure of Large Vascular Gaps," *Plastic and Reconstructive Surgery*, pp 463-68 (1992).

Conklin, B., "Viability of Porcine Common Carotid Arteries in a Novel Organ Culture System", *MS Thesis*, Georgia Institute of Technology, 1997.

Costa, et al., "Increased Elastin Synthesis by Cultured Bovine Aortic Smooth Muscle Cells Subjected to Repetitive Mechanical Stretching," *Faseb J.*, 5: A1609, 7191 (1991).

Fu, et al., "Biorheological Features of Some Soft Tissues Under a Surgical Tissue Expansion Procedure," Biorheological Study on Tissue Expansion, 34: 281-93 (1997).

Han, et al., "Axial Stretch Increases Cell Proliferaiton in Arteries in Organ Culture", *Advances in Bioengineering, ASME, BED* 48:63-64 (2000).

Ippolito, et al., "Histology and Ultrastructure of Arteries, Veins, and Peripheral Nerves During Limb Lengthening," *Clinical Orthopaedics and Related Research*, 308: 54-63 (1994).

Kanda, et al., "Phenotypic Reversion of Smooth Muscle Cells in Hybrid Vascular Prostheses," *Cell Transplantation* 4(6):587-95 (1995).

Kolpakov, et al., "Effect of Mechanical Forces on Growth and Matrix Protein Synthesis in the In Vitro Pulmonary Artery," *Circulation Research, 77*: 823-31 (1995).

Leung et al., "Cyclic Stretching Stimulates Synthesis of Matrix Components by Arterial Smooth Muscle Cells in Vitro," *Science* 191:475-77 (1976).

Moore, et al., "A Device for Subjecting Vascular Endothelial Cells to Both Fluid Shear Stress and Circumferential Cyclic Stretch," *Annals of Biomedical Engineering, 22*: 416-22 (1994).

Ruiz-Razura, et al., "Clinical Applications of Acute Intraoperative Arterial Elongation," *J. Reconstructive Microsurgery, 9*: 335-40 (1993).

Ruiz-Razura, et al., "Acute Intraoperative Arterial Elongation: Histologic, Morphologic, and Vascular Reactivity Studies," *J. Reconstructive Microsurgery, 10*(6):367-73 (1994).

Ruiz-Razura, et al., "Tissue Expanders in Microvascular Surgery Acute Intraoperative Arterial Elongation," *Surgical Forum*, pp. 610-614 (1989).

Stark, et al., "Rapid Elongation of Arteries and Veins in Rats with a Tissue Expander," Plastic & Reconstructive Surgery, 80(4):570-78 (1987).

DEVICE AND METHOD FOR CREATING A VASCULAR GRAFT IN VITRO

CROSS-REFERENCE TO RELATED APPLICATIONS

This is a divisional of U.S. application Ser. No. 09/994,500, filed Nov. 27, 2001, now U.S. Pat. No. 6,641,576, which is a continuation-in-part of U.S. application Ser. No. 09/322,095, filed May 28, 1999, now U.S. Pat. No. 6,322,553. Application Ser. No. 09/994,500 claims benefit of U.S. Provisional Application No. 60/274,702, filed Mar. 9, 2001, and application Ser. No. 09/322,095 claims benefit of U.S. Provisional Application No. 60/087,027, filed May 28, 1998. All of these applications are incorporated herein by reference in their entirety.

BACKGROUND OF THE INVENTION

The present invention is generally in the area of methods and devices to obtain vascular tissue grafts and more specifically in the area of methods and devices to obtain grafts, preferably autologous grafts, prepared from living vascular tissue.

Vascular grafts are commonly used by surgeons to bypass obstructions to blood flow caused by the presence of atherosclerotic plaques. Vascular grafts also are used in other applications such as providing arterial-venous shunts in dialysis patients, vascular repair or replacement and treating aneurysms. Grafts for bypass are often, but not exclusively, used in the coronary arteries, the arteries that supply blood to the heart. The materials used to construct a vascular graft usually are either synthetic or of biological origin, but combinations of synthetic and biological materials are under development. The most widely used biological vascular grafts are autologous saphenous vein or mammary artery. Some common synthetic grafts are made of polytetrafluoroethylene (PTFE) (e.g., GORTEX™) or polyester (e.g., DACRON™). Autologous grafts have generally been used more successfully than synthetic grafts. Autologous grafts remain patent (functional) much longer than synthetic grafts, and saphenous veins often fail in less than five years. The short lifetime of synthetic grafts is especially evident with small diameter (less than 7 mm diameter) grafts, as most small diameter synthetic grafts occlude within one to two years or less.

Small diameter vascular grafts are particularly used in coronary artery bypass surgery. Internal mammary artery (IMA) is the autologous graft of choice, because it typically has a longer life than venous grafts (95% patent at 5 years versus 85% patent at 2 years). Mammary arterial tissue, however, is difficult to harvest, typically is not available in lengths sufficient for multiple bypasses, and its removal can result in problems such as problematic wound healing. Moreover, obtaining sufficient venous tissue for repairing an occluded artery can be problematic in patients with venous conditions such as varicose veins and especially in second or third surgeries in the same patient. Recent literature also suggests that IMA used in bypass procedures either fails soon after transplantation or remains patent indefinitely. See, e.g., Bergsma, et al., *Circulation* 97(24):2402–05 (1998); Cooley, *Circulation* 97(24):2384–85 (1998). Other arteries such as the gastroepipolic, gastric, radial, and splenic also are used in coronary bypass procedures. Moreover, the recent American Heart Association/American College of Cardiology consensus document (Eagle, K. A., et al. "ACC/AHA Guidelines for coronary artery bypass graft surgery: A report of the American College of Cardiology/American Heart Association Task Force on Practice Guidelines", Committee to Revise the 1991 Guidelines for Coronary Artery Bypass Graft Surgery, American College of Cardiology/American Heart Association, *J. Am. Coll. Cardiol.*, 34(4): 1262–347 (1999)) strongly recommends a move to total arterial revascularization.

In some cases, autologous or homologous saphenous vein preserved by freezing or other processes is used.

With people living longer, multiple surgeries are more common. At the same time, open-heart surgery is becoming routine, aided by the development of new, minimally invasive and "off-pump" procedures that have dramatically simplified the surgery and reduced the recovery time.

Development of a longer lasting small-diameter vascular graft is the subject of much academic and industrial research. One current approach is to combine cell culture and biomaterials technologies to make a living, "tissue engineered" graft. This effort, however, is hindered by the requirements of a successful graft: It should be self-repairing, non-immunogenic, non-toxic, and non-thrombogenic. The graft also should have a compliance comparable to the artery being repaired, be easily sutured by a surgeon, and not require any special techniques or handling procedures. Grafts having these characteristics are difficult to achieve. Despite the substantial effort to date and the potential for significant financial reward, academic and industrial investigators have failed to produce graft materials that have demonstrated efficacy in human testing.

Efforts to avoid or minimize the need for vascular grafts for repair of otherwise healthy vascular tissue have been described. For example, Ruiz-Razura et al., *J. Reconstructive Microsurgery*, 10(6):367–373 (1994) and Stark et al., *Plastic & Reconstructive Surgery*, 80(4):570–578 (1987) disclose the use of a round microvascular tissue expander for acute arterial elongation to examine the effects on the tissue of such acute hyperextension. The expander is a silicone balloon that is placed under the vessel to be elongated. The balloon is filled with saline over a very short period, causing acute stretching and elongation of the vessel. The method is purported to be effective for closure of arterial defects up to 30 mm without the need for a vein graft. These techniques are appropriate for trauma, but are not used for restoring blood flow in vessels that are occluded, for example by disease, which are treated by surgically bypassing the obstruction with a graft. The disclosed methods and devices fail to provide an autologous graft or versatile substitute. Moreover, the acute stretching may damage the vessel.

It is therefore an object of the present invention to provide devices and methods for creating natural blood vessel suitable for grafting.

It is another object of the present invention to provide devices and methods for making an autologous blood vessel graft.

It is further object of the present invention to provide devices and methods for creating blood vessel grafts in vivo or in vitro.

These and other objects, features, and advantages of the present invention will become apparent upon review of the following detailed description of the invention taken in conjunction with the drawings and the appended claims.

SUMMARY OF THE INVENTION

Devices and methods are provided for forming a vascular graft by axially distending a blood vessel to stimulate vessel growth. Preferably, the device is implanted, for example using endoscopic techniques, for use in vivo. A portion of a blood vessel (i.e. the donor vessel) then is distended using the device. Preferred donor vessels include the gastroepipolic artery, as well as the internal mammary, femoral, gastric, splenic, and radial arteries. Then, the in vivo distended portion of the donor vessel is excised, for example, at the time of by-pass surgery. In an alternative embodiment, a section of donor vessel is surgically excised from the bypass surgery patient, preferably at the time of by-pass surgery, and then distended in vitro in a medium for cell growth, e.g., in an organ culture system or bioreactor. Where the donor is the recipient of the graft, the result using either approach advantageously is a totally autologous, living vascular graft.

In a preferred embodiment, the device comprises a stretching mechanism which includes (i) a stabilization rod, (ii) a pair of rotatable elements, wherein each rotatable element is rotatably attached to the elongated body and has a channel substantially perpendicular to the axis of rotation, and (iii) a means for rotating each rotatable element to axially distend a blood vessel positioned in the channels of the rotatable elements. The elements can be rotated intermittently, cyclically, or continuously, over a period to distend or elongate the donor vessel.

The rotatable elements can, in one embodiment, comprise a pair of arms extending from a central base, the arms being capable of bending or flexing between a straight configuration and a curved configuration. The straight configuration preferably is used to give the device a narrow profile suitable for endoscopic insertion into a donor patient. The arms can have an inherent spring action, such that the relaxed state of the arms is a curved configuration and wherein the arms will transform from the straight configuration into a curved configuration upon release of one or more releasable fasteners.

In another variation, the rotatable elements each comprise a pair of rounded lobes extending from a central base, the channel extending between each pair of lobes. The lobes can comprise a disk-shaped portion having an outer edge surface distal the axis of rotation of the rotatable element and a substantially flat upper surface distal the stabilization rod. The outer edge surface can include one or more grooves in which a blood vessel or portion thereof can be positioned, supported and guided during the stretching process.

The means for rotating can comprise a torsion spring and a cam mechanism for controlling the rotation position, and/or a prime mover that is mechanically, electromechanically, or hydraulically driven.

The device optionally can include a growth factor or other growth stimulating agent for release in an effective amount to enhance growth of the blood vessel. Such agents may be impregnated into the materials of construction forming the device or can be in the form of a coating or a reservoir device attached to the stretching device.

Also provided is an apparatus for extending a donor blood vessel of a human or animal in vitro. The apparatus includes a chamber containing a quantity of tissue culture growth medium; an inlet cannula extending through a first orifice in the chamber, the inlet cannula having a first end outside of the chamber and a second end positioned inside the chamber; an outlet cannula extending through a second orifice in the chamber, the outlet cannula having a first end outside of the chamber and a second end positioned inside the chamber; and a means, such as a linear motor, for moving the inlet cannula, the outlet cannula, or both, to axially stretch a donor blood vessel secured between the inlet cannula and the outlet cannula in a submerged position in the tissue culture growth medium. In operation, a donor blood vessel is secured by having a first end of the vessel secured to the second end of the inlet cannula and a second end of the vessel secured to the second end of the outlet cannula, thereby forming a conduit through the blood vessel and between the first end of the inlet cannula and the first end of the outlet cannula. Preferably, tissue culture growth medium flows through this conduit.

DETAILED DESCRIPTION OF THE INVENTION

Figure 1:
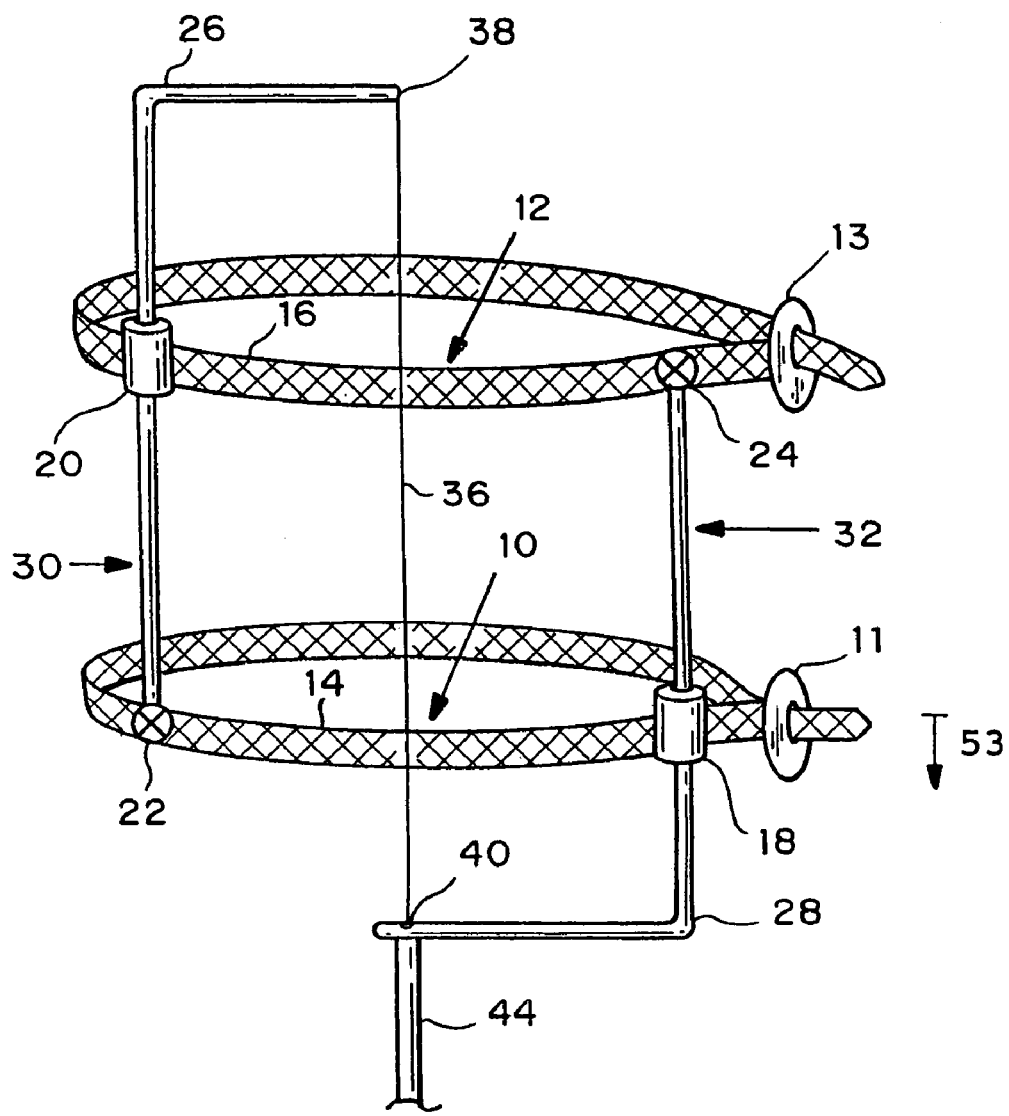
FIG. 1 is a plan view of one embodiment of the device for vessel distension.
Figure 1:
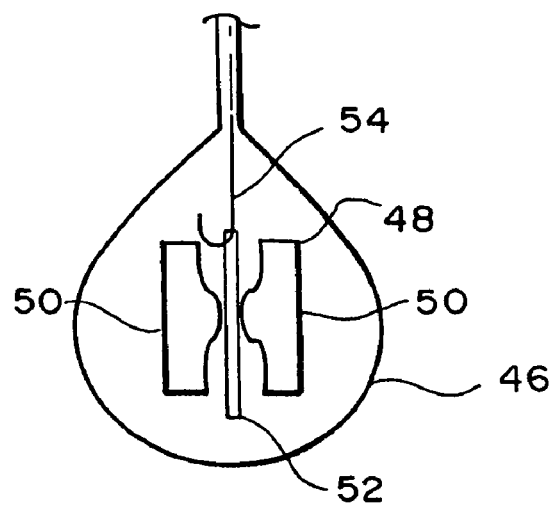

It is known that smooth muscle cells, which dominate the media, the major load bearing layer of the arterial wall, proliferate and increase their production of extracellular matrix in response to mechanical stimulation. It was discovered that this knowledge could be advantageously applied to create an autologous graft of appropriate diameter for coronary bypass or other vascular graft application using a distension device to stimulate angiogenesis. While an autologous graft is preferred, the devices and methods described herein also can be applied to an artery from another human or other animal, including transgenic animals genetically engineered to have tissues that will not be rejected by humans. The distension device can be adapted to operate in vivo or in vitro.

The devices and methods described herein can be used to make allogeneic and xenogeneic vascular grafts, as well as the more preferred autogeneic vascular grafts.

Distension Device

The distension device secures the donor blood vessel at different points on the vessel and then distends or stretches the vessel between those points to form an elongated portion. The elongated portion can then be excised for use as a vascular graft. Stretching can be continuous, cyclical, or intermittent, and can occur rectilinearly, curvilinearly, or in a combination thereof. The stretching can occur between vessel attachment points that are movable relative to one other or in fixed positions relative to one other.

I. Movable Attachment Positions

The device typically includes a stretching mechanism that can be attached by means such as straps or sutures to the donor blood vessel, a means for operating the stretching mechanism to cause the vessel to distend (i.e. extend), and a controller for controlling the operating means.

A. Stretching Mechanism

In a preferred embodiment, the distension device stretching mechanism includes a pair of opposed straps or loops that are fixedly attached to the donor blood vessel such as by sutures. The opposed straps are displaced away from each other over a period of time so that the donor vessel elongates as the straps are displaced. After a period of time, such as when the straps are displaced a pre-determined distance, the section of vessel and the device are removed and the ends of the donor vessel are sutured together if needed.

The device straps should be made out of a biocompatible material such as a synthetic or natural polymer or metal. The straps must be able to be attached to the vessel, for example, using sutures, staples, or adhesion. Examples of suitable material for the straps are polytetrafluoroethylene (PTFE), polyester (e.g., DACRON™), nylon (e.g., DELRIN™), polysulfone, polypropylene, and polyethylene. The strap material preferably is doped to render it radio opaque, so that the stretching process can be monitored using x-ray techniques. The straps can be wrapped in a material that is then attached to the vessel, or they can include perforations or holes to accommodate suturing to the vessel. The straps preferably have a flex strength to support the distending force applied on the stretching mechanism.

The device includes a means to displace the straps away from each other and stretch the vessel. This displacement can be accomplished by any of a variety of techniques. For example, the device can include rods attached to the straps that can be moved to push or pull on the straps to slowly displace the straps from each other. The rods can be moved, for example, by mechanical or hydraulic means.

B. Operating Means

The device includes means to operate the stretching mechanism, preferably including a prime mover and electronic drivers for the prime mover, both of which are preferably implanted. The prime mover can be an electromechanical (active) device, such as a linear-motor that operates the stretching mechanism to push and/or pull the straps away from each other. A rotary motor could also be used to generate the required linear motion, using techniques known in the art. Alternatively, the prime mover can operate hydraulically. An active device generally requires input over time. The prime mover also can be a passive device such as a spring or a combination of a spring and a damper, where stored mechanical energy is used to push and/or pull the straps away from each other.

Linear or rotary piezo micro-motor devices (actuators) deliver small step sizes, small forces, have relatively simple control electronics and inherent force overload protection. Suitable devices are available from a number of vendors, including Micro Pulse Systems, Inc. Parameters of the operating means include the force applied by the stretching mechanism, the rate and direction of movement of the stretching mechanism, the length of time that the stretching mechanism is operated, and the type of stretching applied (e.g., continuous, cyclical, or intermittent).

C. Controller

The controller controls the operating means. In the in vivo distension embodiments, the controller can include a microprocessor that is implanted and that can be activated, programmed, or reprogrammed by an externally applied magnetic or electromagnetic field. The controller also can be activated, programmed, or reprogrammed externally using wires that pass through the skin, or by wireless means for transmitting power or data known in the art wherein wires need not pass through the skin.

One embodiment of the device is shown in FIG. 1. Proximal locking strap 10 and distal locking strap 12 are of adjustable length appropriate for a secure fit around the donor blood vessel to be distended. Blood vessels range from about 0.2 to 2 cm in diameter. The locking straps 10, 12, include a lace 14, 16, respectively, of a biocompatible material, such as DACRON™, that can be secured to the donor vessel, such as by suturing, stapling, or using an adhesive agent. In a preferred embodiment, the laces are designed similarly to the sewing rings of a standard artificial heart valve. Alternatively, a layer of a material, such as a fabric or film, can be attached to the strap so that the vessel can be sutured, stapled, or adhered to the material to hold the strap to the vessel. In another embodiment, the strap includes perforations, holes, or other structural features amenable to suturing or stapling, so that the vessel can be sutured or stapled directly to the strap. The locking straps each have a head 11, 13 with an internal aperture. Preferably, the straps 10, 12 include a plurality of teeth (not shown) that, when the free end of the lace 14, 16 is inserted through the aperture of the head of the strap, it engages the head and prevents the free end of the lace from becoming disengaged, in a manner similar to that of standard pull-ties. Alternatively, the head of the strap can engage the strap if the lace 14, 16 does not cover the entire strap or if the strap includes securing holes or perforations as described above. The straps optionally may be impregnated or coated with one or more growth stimulating agents (e.g., growth factors) that can be released in an effective amount to promote vessel tissue growth during the stretching procedure.

Sliding bearings 18, 20, on straps 10, 12, respectively, and stops 22 and 24, respectively, can be either attached to or integrally formed (during manufacture) with the straps or laces as shown. The bearings and stops are preferably made of the same material as the straps, although other biocompatible materials can be used.

A first push/pull rod 26 is fixedly attached to proximal tie strap 10 at stop 22. A second push/pull rod 28 is fixedly attached to distal tie strap 12 at stop 24. The two push/pull rods are preferably initially not fitted to the locking straps but are easily assembled on the device in vivo after the locking straps are 30 secured around the vessel and sutured or otherwise fixed in place. The push/pull rods slide through the bearings 18, 20 and engage the stops 22, 24. The proximal locking strap 10 including the lace 14, sliding bearing 18, stop 22, and the fixedly attached rod 26 form a first integrated stretch unit 30. The distal locking strap 12 including the lace 16, sliding bearing 20, stop 24, and the fixedly attached rod 28 form a second integrated stretch unit 32. Push/pull rods 26, 28 are preferably made of a rigid material such as stainless steel, titanium or a biocompatible, rigid plastic.

Figure 2:
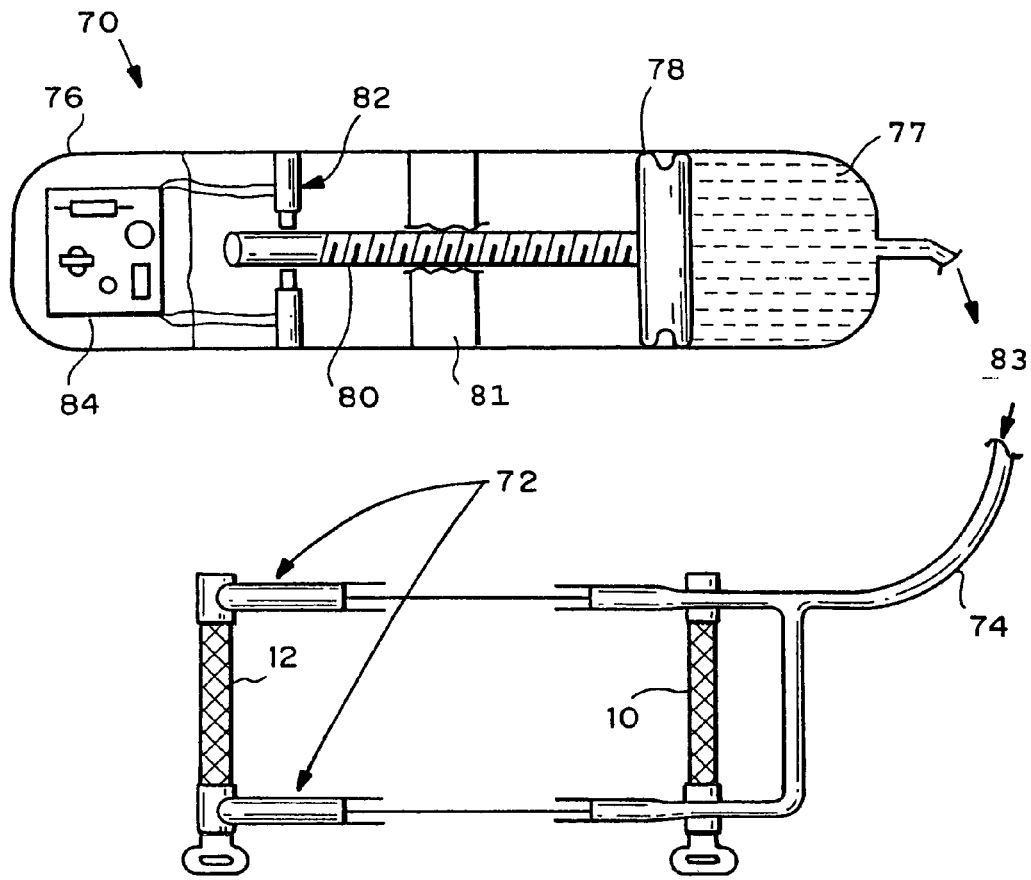
FIG. 2 is a plan view of a second preferred embodiment of the device for vessel distension.

A wire (or cable) 36, preferably stainless steel or titanium, is fixedly attached to first push/pull rod 26 at 38 and passes freely through a hole 40 in push/pull rod 28. The wire 36 then passes freely through the sheath 44 into the prime mover housing 46. The prime mover shown is a piezo-actuator or other linear motor. Those skilled in the art will recognize that several suitable means for pulling the wire or cable are known. For example, the wire or cable can be pulled by a hydraulic cylinder or actuator powered by an implanted pump or by transcutaneous injection of a fluid, such as saline. The wire or cable also could be wound on a rotating reel or attached to a lead screw configured to produce linear motion, wherein either is powered by electric or hydraulic rotary actuators. FIGS. 1 and 2 show two opposing piezo-actuators 50 contained in the housing 46 which can be activated to provide micron-sized step advancement of the driven element 52. Wire 36 is attached to driven element 52 by a hook 54 or other means so that wire 36 is advanced along with driven element 52. Micro Pulse Systems, Inc. makes micro-actuators that are suitable for the device disclosed herein.

As the actuator 48 pulls the wire 36, the first integrated stretch unit 30 is pushed/pulled towards the actuator 48, in the direction of arrow 53. The locking straps are thus displaced away from each other.

The device preferably includes an external driver and controller, which are not shown in the Figures. In a preferred embodiment, the wire can be activated from outside the body once the wire is passed through the skin. Mechanisms outside the body are easier to design and transcutaneous catheters and similar conduits are highly developed.

Figure 9:
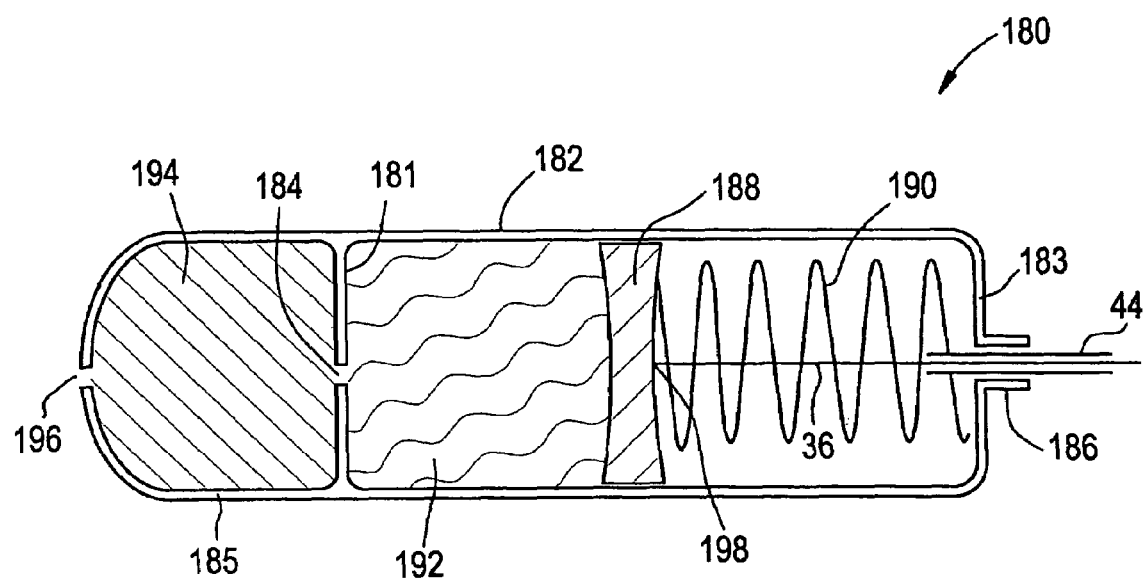
FIG. 9 illustrates a passive power source adaptable to powering the stretching device shown in FIG. 1.

A particularly simple passive device for producing the linear motion needed to pull the wire 36 is illustrated in FIG. 9. The device 180 includes a cylinder 182 having a first orifice 184 at one end 181 and a second orifice 186 at the other end 183, and containing a movable piston 188, a compression spring 190, and working fluid 192. Adjacent the one end 181 is an extension 185 of the cylinder 182, which contains an absorbent material 194 and includes a vent hole 196. The sheath 44 of wire 36 enters the cylinder through second orifice 186, and the wire 36 is attached to the piston 188 at its center 198. The spring 190, which typically is made of stainless steel, titanium or titanium alloy, particularly nickel-titanium, is in compression and pushes piston 188 toward first orifice 184, thereby forcing the fluid 192, typically a biocompatible saline solution, through first orifice 184, where it is absorbed by the absorbent material 194. Representative examples of absorbent materials include synthetic hydrophilic substances, such as certain polymers, or natural materials, such as cellulose. Air or other gas in the interstices of the highly absorbent material 194 that is displaced by the fluid 192 exits from the piston through vent 196. It can be seen that the piston movement provides a continuous driving force and linear motion to the wire or cable 36 in the embodiment shown in FIG. 1. The first orifice 184 can be of a fixed size or a variable size to control the movement of the piston 188. For example, orifices made of piezoelectric or magnetostrictive materials can be made to selectively vary in size by the application of an appropriate electric or magnetic field. The spring 190 can have a linear, nonlinear or constant force deflection characteristic and may consist of multiple springs acting together and designed to produce the required stretching force and motion profile. Those skilled in the art will recognize that this device can be adapted to either push or pull on the cable or wire, depending on the arrangement of the elements.

FIG. 2 illustrates a second embodiment 70 of a device for vessel distension. The hydraulic embodiment uses two miniature, double-acting hydraulic cylinders 72, for example made of stainless steel, titanium or polymer, through which hydraulic force is exerted to stretch the blood vessel by pushing on straps 10. Double acting hydraulic cylinders 72 are connected by a hydraulic line 74 into which fluid flows from the housing 76 which comprise a reservoir of a fluid 77 such as saline. Pressure is generated by a piston 78 driven by threaded rod 80, positioned on a rod support 81, pushing the saline from the reservoir out at 83. Alternatively, pressure may also be generated by means external to the body using a catheter through the skin or by injection into an implanted, subcutaneous port. Such ports are commonly available. The threaded rod 80 is driven using torque generated by frictional engagement with piezo-actuators 82 or by a miniature permanent magnet or other suitable motor. Micro Pulse Systems Inc. supplies piezo-actuators suitable for use in the device. Driver electronics and a power source are indicated by 84. Note that while FIG. 2 shows a hydraulic mechanism wherein only strap 10 is moved, the hydraulic system may be readily adapted by one of skill in the art to exert force on both strap 10 and strap 12.

Alternatively, one skilled in the art could adapt the spring driven piston system illustrated in FIG. 9 to provide hydraulic power to the embodiment illustrated in FIG. 2.

The mechanical or hydraulic stretching mechanism works to move the straps apart slowly over a period of up to several weeks. In one embodiment, the passive driver element illustrated in FIG. 9 may be used to provide a pre-determined stretch over time. In another embodiment, the driver may be pre-programmed to operate autonomously, or the driver may be programmed (or reprogrammed) following implantation by transcutaneous electromagnetic means, based, for example, on x-ray data or other indications of how the process is proceeding. The driver may be simply turned on or off, or may be programmed or reprogrammed by a magnetic field sensing device such as a reed switch (relay) or by other electronic devices or circuits responsive to magnetic or electromagnetic fields. The field is generated by using the external driver control to periodically activate an external source positioned to activate the electronic driver circuit. The external driver control may be pre-programmed to provide a stretch of several centimeters over about one month. Alternatively, cyclic stretching of increasing peak and mean amplitude may be used. Using piezo actuators, activating the driver can produce incremental movements of the mechanical or hydraulic stretching mechanism as small as a few microns. The prime mover is designed to be force limited to preclude overstretching the vessel. Force limitation is inherent if the piezoelectric actuators are used in either embodiment and, in the case of permanent magnetic motors, can be designed into the electronic driver circuit.

II. Fixed Attachment Positions

Figure 4A:
FIGS. 4A and 4B are illustrations of a normal and stretched blood vessel.
Figure 4B:
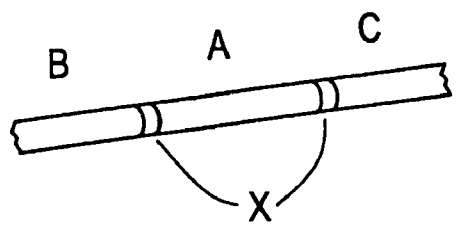

In stretching an artery to stimulate angiogenesis, the blood vessel portion that is beyond the region where the stretching apparatus is attached will be relaxed from its normal stretched state and could possibly be relaxed to the point where it is put in compression, as illustrated in the FIGS. 4A and 4B. FIG. 4A illustrates a blood vessel as it is normally stretched in vivo, and FIG. 4B illustrates how a stretching device having points of contact (X) between vessel sections A and B and between A and C. The stretching device elongates section A while relaxing sections B and C. The consequences of this are unknown, but can be avoided if the blood vessel is stretched between two fixed points, as described herein.

Figure 5A:
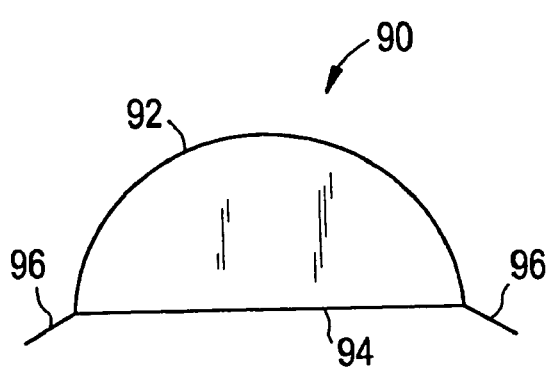
FIGS. 5A–C are front (5A), plan (5B), and side (5C) views of one embodiment of the device for vessel distension using fixed points of vessel attachment.
Figure 5C:
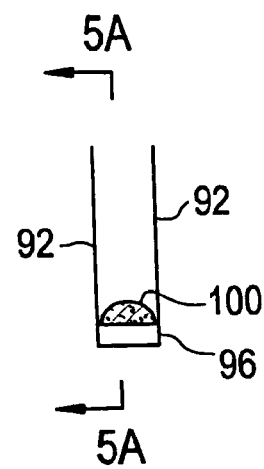
Figure 5B:
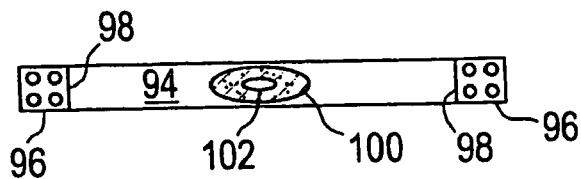

One embodiment of the fixed-point device is shown in FIGS. 5A–C. The device 90 includes two semicircular or similarly shaped thin, yet rigid, plates 92 made of or completely covered by a biocompatible material, such as stainless steel, titanium, titanium alloy, fiber composite, or polymer. The plates are separated and connected so as to remain parallel by a flat rectangular strip of similar material 94. The ends of the strip 96 are perforated or otherwise formed to accept surgical sutures or other means (e.g., adhesive) known in the art to secure a blood vessel to the strip at its ends. The ends 96 are also flexible and easily bent, but without breaking, about axis 98 shown. The device can be formed from a single appropriately shaped thin plate. The area between the plates contains at least one inflatable balloon 100, which may be formed from silicone, rubber, elastomeric polymers, or any other highly deformable biocompatible material. As the balloon 100 is inflated, it fills the space between the two thin plates 92 without significantly changing the spacing between the two plates 92, since the plates 92 and strip 94 are sufficiently rigid to ensure this. Inflation of the balloon 100 can be accomplished using at least one access port 102, through which a fluid, such as saline, is injected, for example, through a needle or catheter connected to a syringe or similarly functioning device. The inflation process can occur through the skin. The balloon is designed and attached to the strip in such a manner that, at full inflation, it assumes more or less the shape of the space between the two plates confining it.

An alternative stretching mechanism is provided by hydrophilic or chemically reactive synthetic substances (e.g., various polymers) or other natural materials (e.g., cellulose) known to significantly expand their dry volume when activated as by exposure to fluid or possibly other stimuli (e.g., heat, radiation or various chemical agents). Such materials are available in foamed, fiber or other forms, any of which may be adapted by one of skill in the art to effect the balloon inflation described herein. One or more of these materials can be placed inside the balloon and expanded by the controlled addition of a fluid or chemical agent, such as by injection into the balloon, which causes the materials to expand, inflating the balloon, in much the same way as simply pumping saline or another fluid into the balloon as described above. The material could also be otherwise encapsulated or separated from the stimuli to control its means and rate of activation. For example, expandable material could be provided with a degradable coating or other timed-release mechanism, and such mechanisms can be readily adapted from those used in controlled drug delivery. Alternatively, the balloon can be omitted, and the hydrophilic or other volume expanding material can simply be placed between the two plates in such a manner that exposure to body fluids or another appropriate stimulus causes the material to expand and fill the area between plates.

III. Combination Fixed/Movable Attachment Positions

Figure 7A:
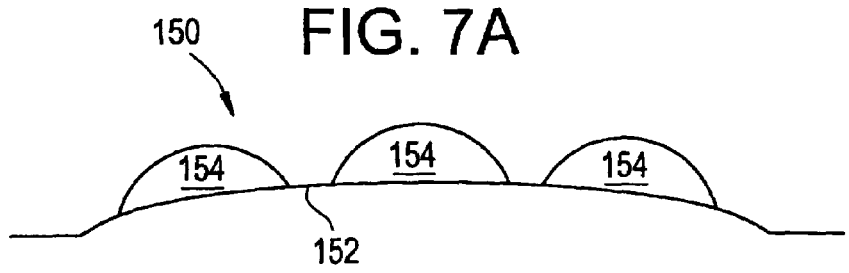
FIGS. 7A–C are front (7A), plan (7B), and side (7C) views of one embodiment of a device for both rectilinear and curvilinear vessel distension.
Figure 7C:
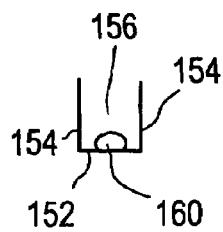
Figure 7B:
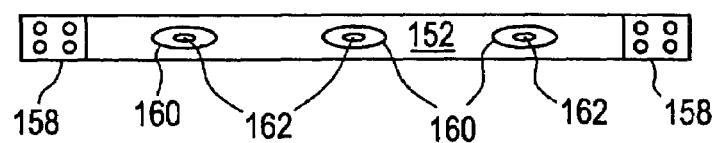

Other embodiments combine rectilinear and curvilinear stretching. One such embodiment is a slightly modified version of device 90 (shown in FIGS. 5A–C) and is illustrated in FIGS. 7A–C. The device 150 includes strip 152, that is formed much like strip 94, except that it is formed in a slightly curved or angled configuration and includes at least one, and preferably several, plates (or tabs) 154, positioned at or near the long edge of the strip 152 so as to form a channel 156. Strip 152 has flexible ends 158 for attachment to the blood vessel. A blood vessel is placed in channel 156 and attached to the strip 152, like described for strip 94, wherein plates 154 serve to hold the blood vessel in place. The space between the plates contains one or more (three are shown) inflatable balloons 160, which are like balloon 100 described above. Inflation of the balloon(s) can be accomplished using at least one access port 162, also as described above.

Method for Distending a Blood Vessel

The distension device can be adapted to operate in vivo or in vitro, that is to distend a portion of a blood vessel in vivo or following its excision from the body and subsequent placement in a medium for cell growth. As used herein, the phrase "medium for cell growth" includes any in vitro system for facilitating cell division, extra-cellular matrix formation, and growth of vessel tissue. For example, the distension device can be attached to an excised portion of donor vessel and submerged in a medium for cell growth in a temperature-controlled container. As described in Example 1, it has been shown that distension in an organ culture (e.g., a bioreactor) significantly stimulates cell division, and can be simple to control. See, for example, U.S. Pat. No. 5,899,936 to Goldstein; U.S. Pat. No.5,879,875, to Wiggins, et al.; and U.S. Pat. No. 5,888,720 to Mitrani, which describe techniques for organ and tissue culture which can be adapted to the methods described herein.

I. Operating the Movable Positions Device

The method for distending a donor blood vessel can include attaching a stretching mechanism to the donor vessel and operating the stretching mechanism to stretch the donor vessel. In one embodiment, the method involves using a device wherein a pair of straps are fixedly attached to the donor vessel and moved away from one another so that the portion of the vessel between the straps is distended. The distended portion can then be excised and used as a graft. Grafts for coronary by-pass surgery are typically between about 10 cm and 15 cm in length, whereas grafts for by-pass in the peripheral circulation are typically about 25 cm or more in length. Those of skill in the art can readily optimize the rate of vessel distension. Distension rates can be linear or nonlinear, and may average, for example, between about 5 and 10 mm/day.

Figure 3:
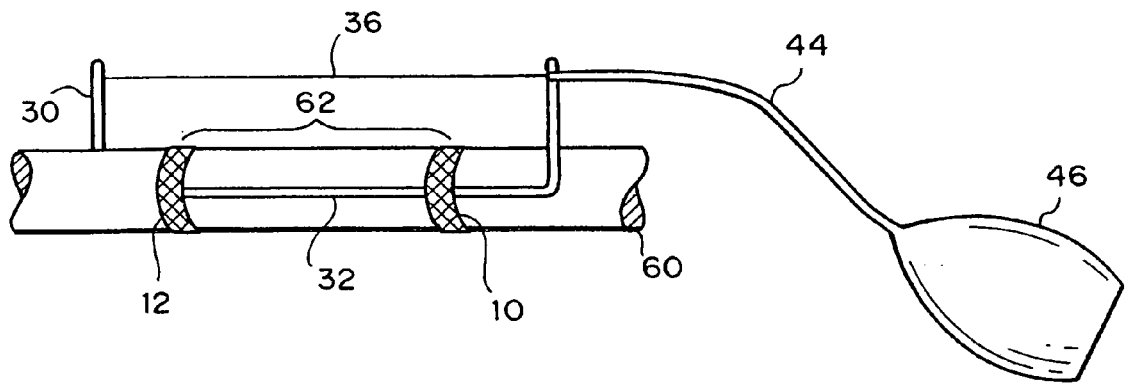
FIG. 3 is a side elevational view of the distension device shown attached to a donor blood vessel.

One embodiment of the method is illustrated in FIG. 3, wherein a device (e.g., the one shown in FIG. 1) is attached to a donor blood vessel 60. The device can be assembled before or at the time of implantation. Straps 10, 12 are engaged to encircle the donor vessel and are then sutured in place. Push/pull rods 30, 32 are attached to the straps. Wire 36, and the housing assembly shaft 44, and housing 46 (containing the actuator) are attached to the device. Preferably, the active prime mover is implanted complete with its drive circuit and a minimal power source. Alternatively, a passive device, such as described above, can be used. As either device is operated, the section of vessel 60 between the straps 10, 12, indicated by 62, stretches.

II. Operating the Fixed Positions Device

Figure 6A:
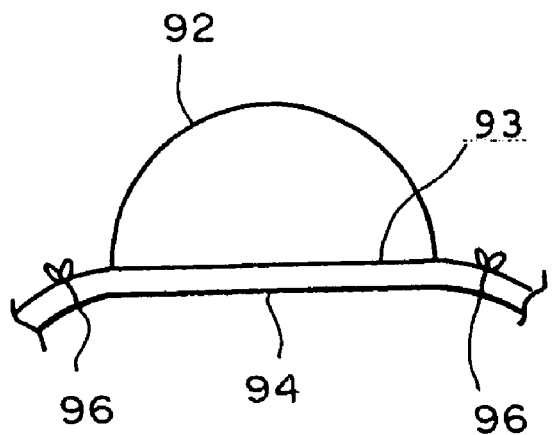
FIGS. 6A–C are diagrams showing vessel distension using a preferred embodiment of the device having points of vessel attachment that are fixed relative to one another.
Figure 6B:
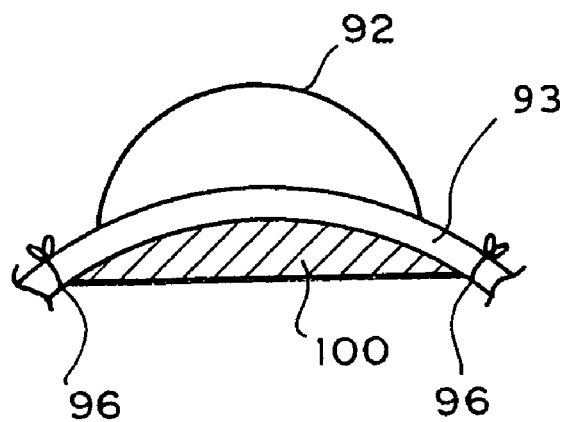
Figure 6C:
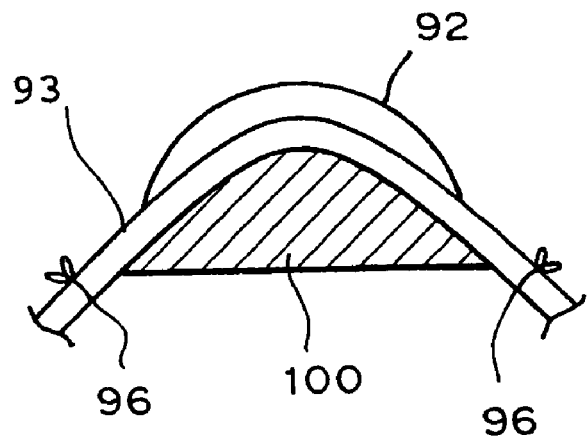

The device using fixed attachment positions is preferably operated as shown in FIGS. 6A–C, which show a cross-sectional view (a—a) of the device in FIGS. 5A–C, at increasing degrees of vessel distention occurring with increasing inflation/expansion of the balloon/expanding material. In operation, the target blood vessel 93 is placed between the two plates 92, resting on the uninflated balloon 100 (or unexpanded material) and secured to the flexible ends 96 of the strip 94, for example by sutures or other suitable means (FIG. 6A). As the balloon is inflated (or the material expanded), the blood vessel 93 is stretched (FIG. 6B), between the two fixed ends 96 and continues to stretch as the space between the two plates is filled (FIG. 6C), without the possibility of reducing the tension in or compressing the blood vessel 93 not between the points of attachment.

III. Operating the Combination Fixed/Movable Positions Device

Figure 8A:
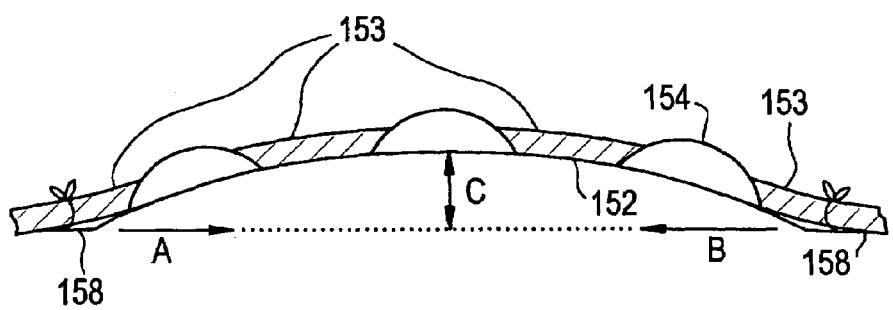
FIGS. 8A–B are diagrams showing vessel distension using one embodiment of the device for both rectilinear and curvilinear vessel distension.
Figure 8B:
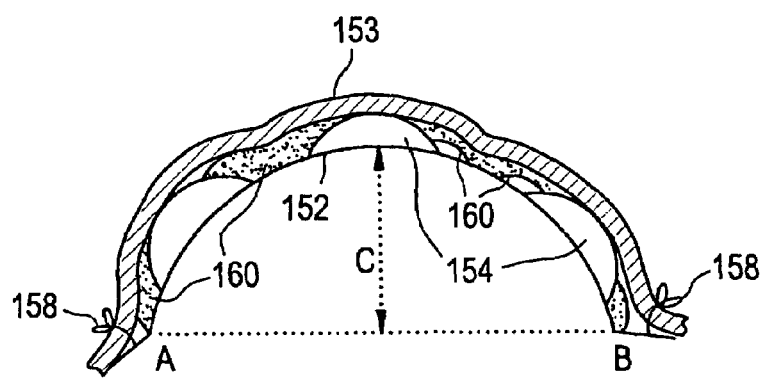

The device using the combination of fixed and movable attachment positions is preferably operated as shown in FIGS. 8A–B. FIG. 8A shows a blood vessel attached to the device before application of the bending force (i.e. before distension). FIG. 8B shows the device and blood vessel following application of the bending force, wherein strip end A is drawn towards strip end B. The device can be, for example, device 150 described above.

In operation, the target blood vessel 153 is first placed in the channel formed by plates 154, resting on the uninflated balloon 160 and secured to the flexible ends 158 of the strip 152, for example by sutures or other suitable means. The ends 158 of the strip 152 are then drawn towards each other by mechanical or other forces to cause strip 152 to bend or flex, thereby stretching the blood vessel 153. The ends can be drawn towards one another by any suitable means, including a mechanical or magnetic force, or by a differential expansion effect, for example where the strip consists of laminates of materials that contract or expand differently from one another when exposed to a stimulus, such as heat (thermal expansion) or water (e.g., top layer of strip hydrophilic while bottom layer hydrophobic). The mechanical means can include, for example, the linear or rotary piezo micro-motor devices described herein. As the strip 152 is bent, distance C increases and distance AB decreases, causing the section beyond either A or B to be stretched in a rectilinear manner.

Additionally, as balloon 160 is inflated (or the material expanded), the blood vessel is stretched between the two ends 158 and continues to stretch as the space in the channel defined by plates 154 is filled. Thus, the section of blood vessel between ends A and B is stretched in a curvilinear manner. The two modes of stretching can occur simultaneously, one after another in either order, or any combination thereof.

IV. In Vitro Operation

Currently, a short segment of blood vessel can be salvaged during conventional bypass surgery and an in vitro organ culture or bioreactor system can be used to grow sufficient graft tissue for a second surgery. Such surgeries represent about 30% of all bypass operations. The methods and devices described herein can be adapted to work with such surgeries, to increase the length of graft material and/or to reduce the required length of the salvaged segment. Stretched blood vessels can be effectively preserved for bypass surgery, for example, using known cryogenic or freeze-drying techniques.

Figure 10:
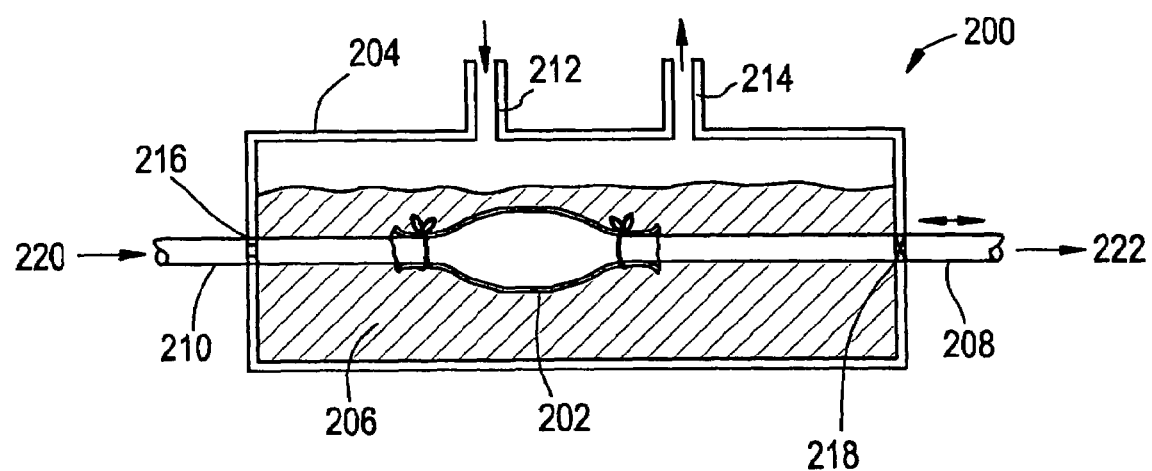
FIG. 10 illustrates an organ culture or bioreactor system modified to allow axial extension of a blood vessel contained therein to induce growth.

FIG. 10 illustrates an organ culture or bioreactor system 200 modified to accommodate the need to stretch a blood vessel to induce growth. A donor blood vessel 202 is connected at its two ends to first and second cannulas 208 and 210 so that it is continuously immersed in a suitable tissue culture medium 206 at physiological temperature. A representative example of a tissue culture medium consists of DMEM (Sigma D1152), sodium bicarbonate (3.7 g/L, Sigma), L-glutamine (2 mM, Sigma), antibiotic-antimycotic solution (10 ml/L, Gibco), calf serum (CS 10%, Integren) and, possibly, Dextran (5% by weight, MW 282,000 Sigma). The medium 206 is contained a liquid-tight chamber 204, having gas inlet aperture 212 and gas outlet aperture 214, to permit gases, such as a mixture including oxygen and carbon dioxide, to enter the chamber 204, exchange gases with the medium 206, and then exit the chamber 204. The chamber 204 may also include one or more openings (not shown) to permit changing or replenishing of the medium 206. Second cannula 210 is generally fixed and passes into the chamber 204 through seal 216, whereas first cannula 208 passes through a sliding seal 218 and can move linearly to effectively stretch or relax the blood vessel 201. The linear motion of the cannula or the force exerted on the blood vessel can be controlled by a linear motor or by means such as described herein. Tissue culture medium, at physiological temperature and pressure (including pulsatility), preferably is continuously introduced into cannula inlet 220, flows through blood vessel 202, and then exits from cannula outlet 222. This internal medium also should be exposed to carbon dioxide and oxygen gases so that gas exchange can occur.

In various embodiments, the apparatus includes means for moving the inlet cannula, the outlet cannula, or both cannula to axially stretch a donor blood vessel secured between the inlet cannula and the outlet cannula in a submerged position in the tissue culture medium. The inlet cannula, the outlet cannula, and the donor blood vessel are secured together to form a conduit through which the tissue culture medium can flow. In one embodiment, a primer mover is operably connected to the inlet cannula, the outlet cannula, or both cannula, to axially stretch the donor blood vessel. The primer mover can be mechanically, electromechanically, or hydraulically driven. In one embodiment, either the inlet cannula or the outlet cannula is in a fixed position in the chamber, and the other cannula is moveable in a linear direction. The means for moving either or both of the cannula can include a controller for moving the cannula in a continuous or intermittent manner.

Application of the Distension Devices and Methods

The present devices and methods are useful for forming a vascular graft by axially stretching (i.e. distending or extending) a donor blood vessel to stimulate growth. This stretching can performed in vivo or in vitro.

The devices and methods can be sized to stretch blood vessels of essentially any size and located in or excised from a variety of sites in the body of the patient or donor or animal. Preferred blood vessels include, but are not limited to, the internal mammary arteries, the gastroepipolic artery, the gastric artery, the radial artery, the femoral artery, and the splenic artery. Other arteries and veins may also be suitable blood vessels for use with the methods and devices.

In a preferred embodiment of the in vivo distension method, the device is implanted, for example using endoscopic techniques, in the patient and vessel distension effected over a period of time. Then the site of implantation is reexposed, all or a portion of the donor blood vessel section (e.g., vessel segment 62 in FIG. 3) is removed and the device is explanted. The ends of the donor vessel can then be sutured end to end to repair the donor vessel, as is commonly done in vascular repair without complication. Some blood vessels used for coronary bypass surgery, such as the gastroepipolic and radial arteries, can be removed with minimal morbidity such that repair is unnecessary. The removed blood vessel section is then ready for use as a graft in a patient in need thereof, who preferably is the same patient supplying the donor vessel.

In a preferred embodiment of the in vitro distension method, a portion of donor blood vessel (e.g. shorter than that needed for a graft) is surgically excised from the patient in need of the graft, and then the vessel portion is stretched over a period of time in vitro in a medium for cell growth, for example, as in a bioreactor. All or a portion of the distended vessel is then ready for use as a graft in the patient. Where the donor is the recipient of the graft, the result using either approach advantageously is a totally autologous, living vascular graft.

Preferred Embodiments

In a preferred embodiment of the device, the stretching mechanism is not actually attached to the blood vessel and is therefore easier to use, as no suturing of the device to the vessel is required. The device also preferably is enclosed so that the possibility of tissue adhesions to soft tissue and/or infiltration by body fluids—potential problems with essentially any implanted device—is minimized. The device also preferably includes a growth stimulating agent, such as a growth factor, to stimulate blood vessel tissue growth. For in vivo applications, the device also preferably is sized and shaped to facilitate minimally invasive implantation, such as by endoscopic insertion.

Preferably, the device comprises a stretching mechanism which includes (i) a stabilization rod, (ii) a pair of rotatable elements, wherein each rotatable element is rotatably attached to the stabilization rod and has a channel substantially perpendicular to the axis of rotation, and (iii) a means for rotating each rotatable element to axially distend a blood vessel positioned in the channels of the rotatable elements. As used herein, the term "substantially perpendicular" includes angles between 0 and 20°, preferably between about 0 and 10°, and more preferably between 0 and 5°.

Figure 11A:
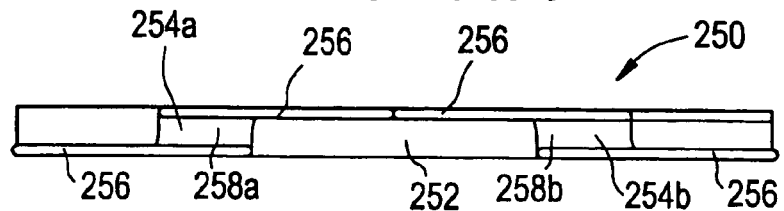
FIGS. 11A–E are plan views of a preferred embodiment of a device employing a pair of rotatable elements that provide both rectilinear and curvilinear vessel distension.
Figure 11B:
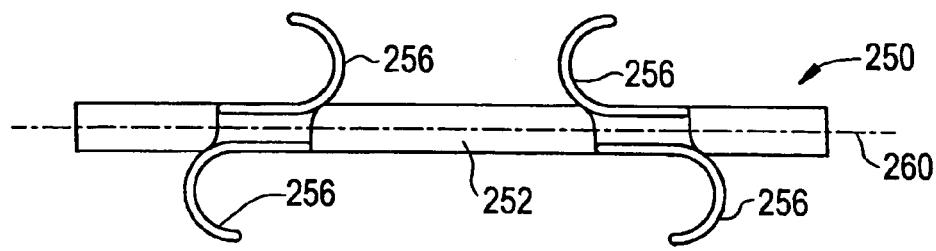
Figure 11C:
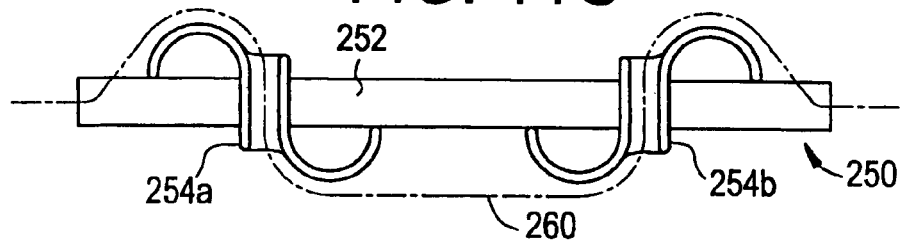

One variation of such an embodiment is shown in FIGS. 11A–E as device 250. The device 250 includes a stabilization rod 252 and two rotatable elements 254a and 254b, which are rotatably attached to the stabilization rod 252. Rotatable elements 254a and 254b each include a pair of arms 256 capable of bending or flexing between a straight and a curved configuration, as shown by comparing FIGS. 11A and 11B. FIG. 11A illustrates the device 250 in a collapsed form, which provides a profile that is well suited to endoscopic insertion. FIG. 11B shows the device 250 in an expanded form as it would appear after insertion into the body but prior to use in stretching a blood vessel. The elements of this embodiment can be fabricated using suitable materials and methods to accomplish the transformation of shape shown. The arms 256 preferably can be maintained in a collapsed, straight profile (FIG. 11A) with one or more releasable fasteners (not shown) securing the arms to one another or to the stabilization rod, so that the device 250 can be easily implanted. Representative examples of releasable fasteners include thin breakable connections, bonds, or welds, as well as screws, clamps, and hooks. A removable sleeve that snugly fits around the arms and stabilization rod may also serve as a fastener to hold the arms in a collapsed profile. Such a sleeve could simply be slid off of the stabilization rod following insertion to release the arms. The shape change of the arms 256 is preferably due to a spring action inherent in the material of construction of the arms 256, such that, upon release (e.g., upon breaking of the connection, bond, or weld), the arms will transform from the straight configuration (FIG. 11A) to the curved configuration (FIG. 11B). Such a transformation can occur as a result of the elastic restorative forces normally exhibited in most metals and polymeric materials, forces that could be made, by one skilled in the art, to straighten a curved element formed from these materials. Nickel-titanium alloys, which exhibit super-elastic and shape-memory effects, are particularly suitable. Shape memory nickel-titanium alloys and certain polymeric materials can be fabricated to change shape from straight to curved as the device warms to body temperature after it is inserted. Examples of shape memory polymers are described, for example, in PCT WO 99/42528 and U.S. Pat. No. 6,160,084, which are incorporated herein. Methods for forming the elements of the device are well known to those skilled in the art.

Figure 11D:
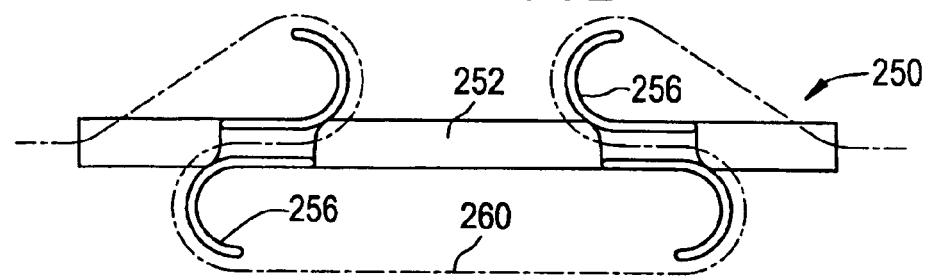
Figure 11E:
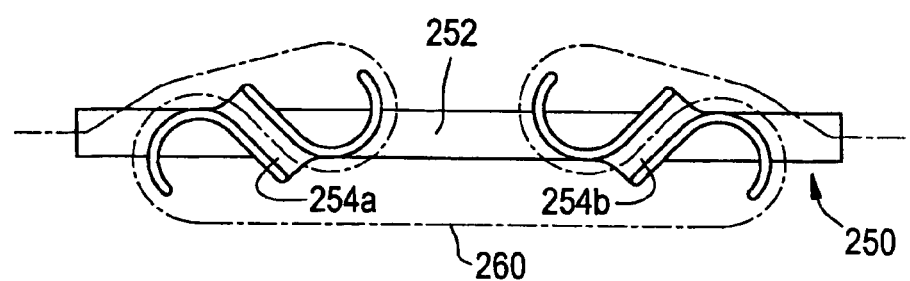

FIGS. 11B–11E illustrate use of the device 250 with a blood vessel 260 (represented as a broken line). These figures also illustrate the rotational movement of the rotatable elements 254a and 254b. First, the blood vessel 260 should be threaded into element channels 258a and 258b of rotatable elements 254a and 254b, respectively, and then the rotatable elements 254a and 254b are rotated to cause the vessel 260 to stretch, in a combination of rectilinear and curvilinear stretching. The vessel 260 is frictionally engaged with the rotatable elements 254 and arms 256, and need not be sutured or otherwise attached to the device 250. To better grip the blood vessel 260, the arms 256 can have a suitably curved cross section or groove similar to the grooves described in the embodiment shown in FIG. 12B. FIGS. 11D and 11E show successive rotation of rotatable elements 254a and 254b, as well as the associated lengthening of blood vessel 260.

Figure 12A:
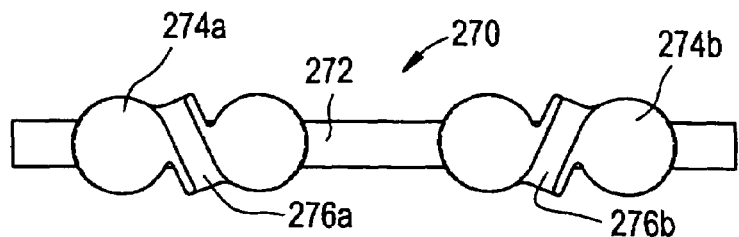
FIGS. 12A–F are plan views (FIGS. 12A–B, 12D–F) and a side view (FIG. 12C) of another preferred embodiment of a device employing a pair of rotatable elements which provide both rectilinear and curvilinear vessel distension.
Figures 12B, 12C:
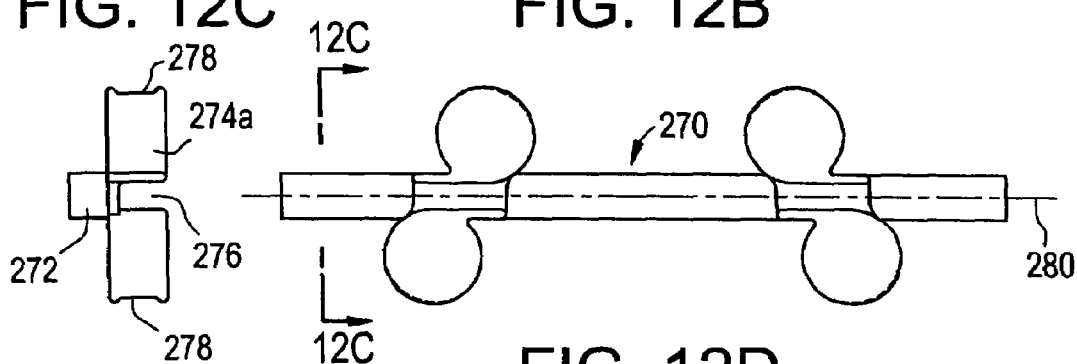
Figure 12D:
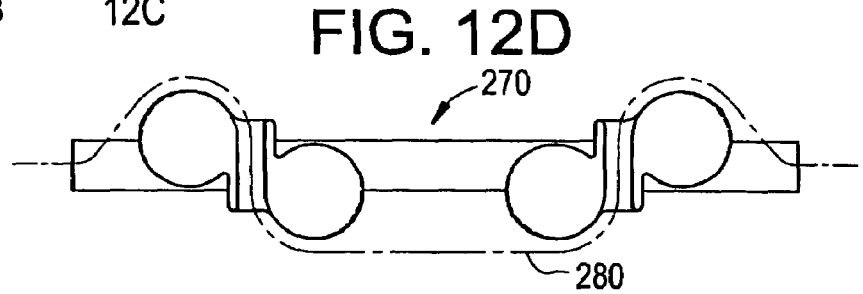
Figure 12E:
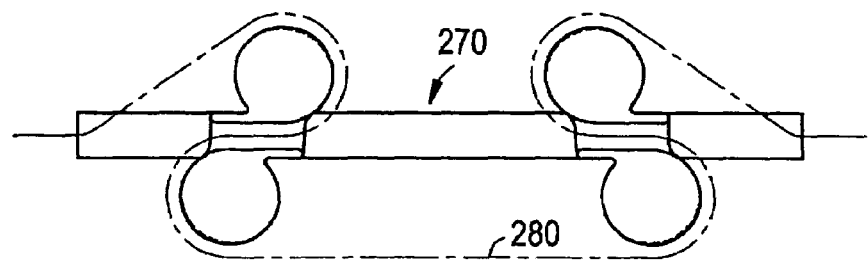
Figure 12F:
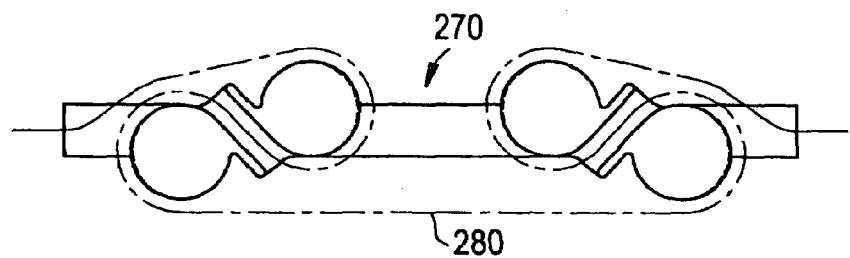

Another variation of a preferred embodiment is shown in FIGS. 12A–F as device 270. The device 270 includes a stabilization rod 272 and two rotatable elements 274a and 274b, which are rotatably attached to the stabilization rod 272. The rotatable elements 274a and 274b each have a pair of rounded lobes extending from a central base, thereby providing a shape with a smooth, rounded profile to permit insertion with an endoscope, while not requiring the device to have a collapsed configuration as in device 250. FIG. 12A illustrates the device 270 in its insertion profile. FIG. 12B shows the device 270 in an expanded form as it would appear after insertion into the body, with rotatable elements 274a and 274b rotated slightly to align channels 276a and 276b with the stabilization rod 272, rendering the device 270 ready for threading with a blood vessel 280 (represented as a broken line). The elements of this embodiment can be fabricated using suitably rigid materials and known fabrication methods. Materials such as stainless steels, titanium, titanium alloys or biocompatible polymers are suitable. Methods for forming the elements of the device are well known to those skilled in the art. FIG. 12C illustrates a side view of rotatable element 274a along line d—d in FIG. 12B. Rotatable elements 274a/b include grooves 278 at its periphery, as shown in FIG. 12C, to support and guide the blood vessel 280, keeping it from slipping off of the rotatable elements 274a/b as the rotatable elements 274a/b rotate. Such grooves are optional.

FIGS. 12B and 12D–12F illustrate use of the device 270 with a blood vessel 280. These figures also illustrate the rotational movement of the rotatable elements 274a and 274b. After blood vessel 280 is threaded into element channels 276a and 276b of rotatable elements 274a and 274b, respectively, the rotatable elements 274a and 274b are rotated to cause the vessel 280 to stretch. More rotation will yield more vessel stretching, and thus a greater length of vessel graft material provided.

Figure 13A:
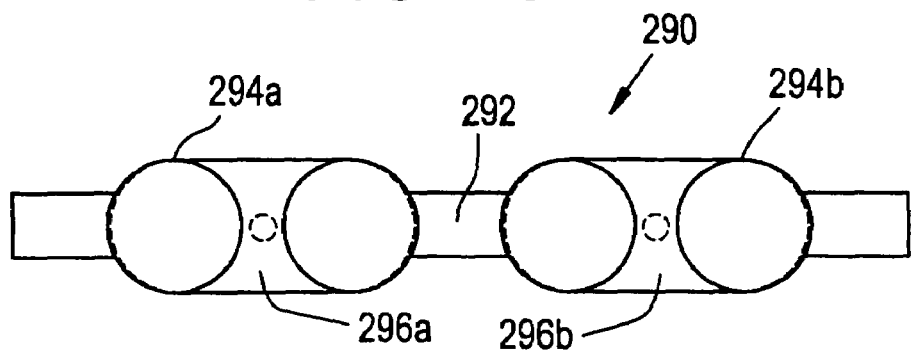
FIGS. 13A–E are plan views (FIGS. 13A–D) and a side view (FIG. 13E) of another preferred embodiment of a device employing a pair of rotatable elements which provide both rectilinear and curvilinear vessel distension.
Figure 13B:
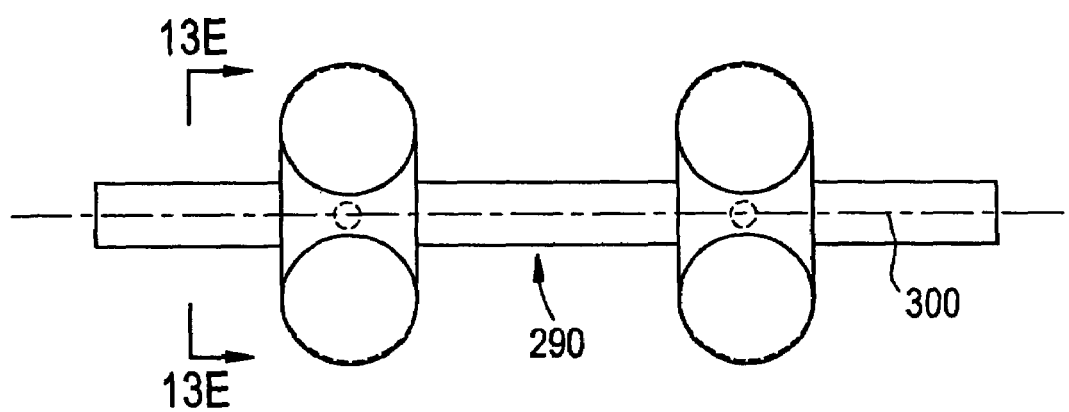
Figure 13C:
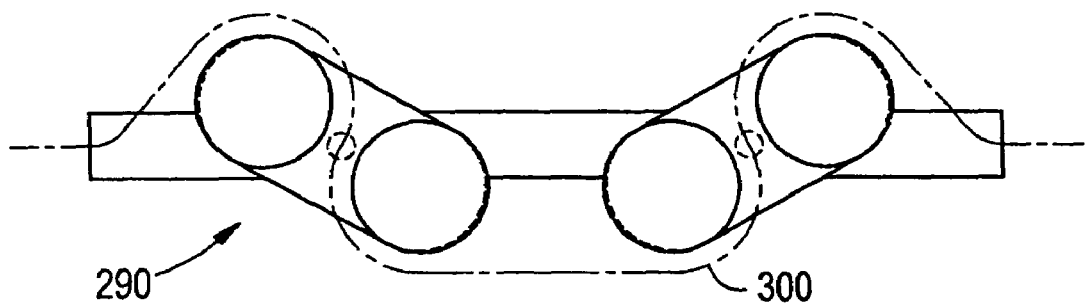
Figure 13D:
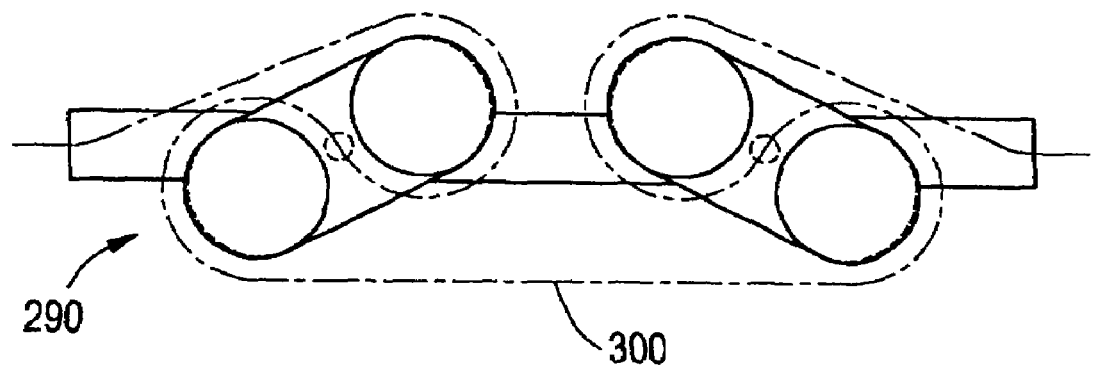
Figure 13E:
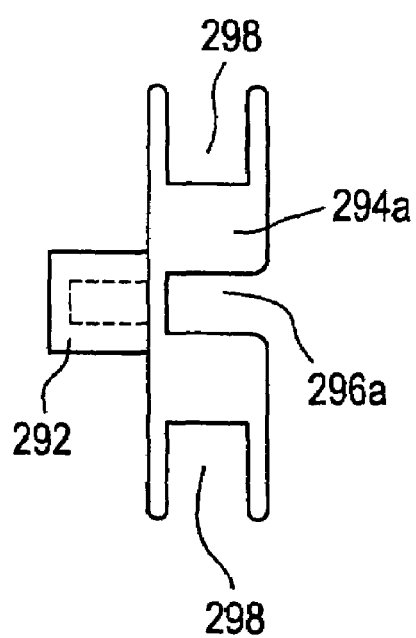

Yet another variation of a preferred embodiment is shown in FIGS. 13A–E as device 290. The device 290 includes a stabilization rod 292 and two rotatable elements 294a and 294b, which are rotatably attached to the stabilization rod 292. The rotatable elements 294a and 294b are, like elements 274, shaped to have a smooth, rounded profile to permit insertion with an endoscope; however, elements 294 are in a shape that typically should be somewhat simpler to manufacture. FIG. 13A illustrates device 290 in is insertion profile. FIG. 13B shows the device 290 in an expanded form as it would appear after insertion into the body, with rotatable elements 294a and 294b rotated slightly to align channels 296a and 296b with the stabilization rod 292, rendering the device 290 ready for threading with a blood vessel 300 (represented as a broken line). The elements of this embodiment also can be fabricated using suitably rigid materials and known fabrication methods similar to those described for the devices illustrated in FIGS. 11 and 12. FIG. 13E illustrates a side view of rotatable element 294a along line e—e in FIG. 13B. Rotatable elements 294a/b includes grooves 298 at its periphery, as shown in FIG. 13E, to support and guide the blood vessel 300, keeping it from slipping off of the rotatable elements 294a/b as the rotatable elements 294a/b rotate.

Figure 14:
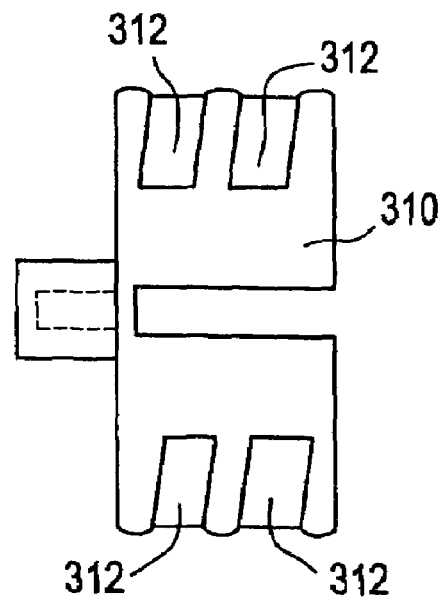
FIG. 14 is a side view of a variation of a preferred device, wherein the rotatable element includes multiple grooves for guiding a blood vessel during the rotating and stretching process.

FIG. 14 shows a variation of a rotatable element 310, which is provided with multiple grooves 312 for supporting and guiding a blood vessel. As can be seen, the grooves 312 are in a threaded arrangement to permit multiple revolutions of the rotatable element 310, rendering a device capable of further increasing the length of blood vessel produced by stretch induced growth.

In all of these preferred embodiments and variations, the stabilization rod preferably is a substantially rigid, elongated body or structure. The devices are designed so that their cross-sectional dimensions facilitate endoscopic implantation, preferably using available hardware. Standard trocars for endoscopic access range in size to 25 mm. Device length is influenced by choice of artery, length of graft produced, and other factors. The expected length is between about 4 cm and 20 cm.

While two rotatable elements are shown and preferred, the device also can work with one or three or more rotatable elements. Additional rotatable elements can be added, by one skilled in the art, if needed to produce a single, more complex, device capable of additional lengthening. When such additional lengthening is necessary, it can be more easily achieved using multiple devices as described.

The rotational movement of the rotatable elements can be driven by a wide variety of forces and driver means known in the art. For example, the means for rotating the rotatable elements can include a torsion spring and a cam mechanism for controlling the rotation position. The spring and cam preferably are situated within the stabilization rod. The rotation also may be conducted using mechanical, electromechanical, hydraulic, or other means known for controllably rotating structures relative to a base structure, for example, by adapting one or more of the means described above. In a preferred embodiment having two rotating elements, each rotates in opposite directions from one another. Additional (dynamic) stretching of a blood vessel can be achieved by variable longitudinal placement of the elements from one another along the stabilization rod. For example, one of the rotatable elements can be a floating mechanism that can be moved along the stabilization rod away from the other, fixed, rotatable element, thus providing additional stretch to the blood vessel segment between the rotatable elements.

Additional means for producing the required rotational motion include directly driving the rotatable elements using suitably controlled rotary micromotors. Common mechanical elements, such as racks and pinions, can be combined to convert linear to rotary motion. Such mechanisms can be driven by linear or geared rotary motors or by elastic stored energy, such as the energy stored in a tension or compression spring, or by hydraulic means or by some combination of these means. Activation of one or both of the rotatable elements, either synchronously or asynchronously, continuously or intermittently, can be used as most appropriate for a particular embodiment.

The methods and devices described herein optionally can include growth factors or other growth stimulating agents (e.g., hormones) to further enhance blood vessel growth. For example, such growth stimulating agents can be delivered to the blood vessel by impregnating the materials forming the device or by providing a suitable coating or reservoirs in the device that can contain and controllably release such agents during the extension process. Examples of growth factors include vascular endothelial growth factor (VEGF), endothelial cell growth factor (ECGF), basic fibroblast growth factor (bFGF), and platelet derived growth factor (PDGF). Biocompatible polymeric materials for controlled release that are known in the art for drug delivery (see e.g., U.S. Pat. No. 5,879,713 to Roth et al.) can be adapted for use with the devices described herein. The devices and methods also can be used in combination with external electric, magnetic, or electromagnetic fields applied as a growth stimulus (see e.g., U.S. Pat. No. 4,846,181 to Miller).

The devices also can optionally include appropriate drugs (e.g., therapeutic or prophylactic agents) impregnated into or coated to structural components, for example to minimize infections, inflammatory reactions, scar tissue formation, adhesion formation, and/or other adverse tissue reactions. For example, where tissue growth is to be avoided, certain antifibrotic agents may be present, such as 5-fluourouracil or mitomycin. The device may be more generally provided with coatings that are antibiotic or anti-inflammatory.

The devices also can be enclosed in a suitable sheath to limit adhesion formation and/or infiltration by body fluids while implanted in vivo, or be impregnated or coated with materials selected to reduce adhesion formation as known in the art. Examples of such coating materials include, but are not limited to, parylene, polytetrafluoroethylene (e.g., TEFLON™) and chromium (e.g., ME-92™, Armoloy Corp.), which can be used to coat a variety of other metal and polymer substrates.

The devices and methods of use thereof described herein are further described by the following non-limiting examples.

EXAMPLE 1

In Vivo Vessel Stretching to Stimulate Cell Division

Leung et al., *Science* 191:475–77 (1976) showed that cyclic stretching stimulates synthesis of matrix components in arterial smooth muscle cells in-vitro. Subsequent studies in arterial tissue have been limited to the effects stretching on cells attached to a membrane in cell culture (see, for example, Birukov, et al., *Molecular & Cellular Biochem.*

144:131–39 (1995); Costa, et al., *FASEB J.* 5:A1609–7191 (1991)) or in a vascular graft construct (Kanda, et al., *Cell Transplantation* 4(6):587–95 (1995)). No known studies, however, have analyzed the effect of stretch on cells in intact vessel walls. Therefore, a study was made of porcine carotid arteries in an organ culture system developed by Conklin (Conklin, B. *Viability of Porcine Common Carotid Arteries in a Novel Organ Culture System* MS Thesis, Georgia Institute of Technology, 1997), in order to determine the effect of axial stretching on smooth muscle cell division in an intact vessel. See also Han, H. C., Vito, R. P., Michael, K., Ku, D. N., "Axial Stretch Increases Cell Proliferation in Arteries in Organ Culture", *Advances in Bioengineering, ASME, BED* 48:63–64 (2000).

Left and right external carotid arteries were obtained at slaughter, one for testing and the other serving as a control. Both vessels were immersed in cell culture media containing DMEM (Sigma D1152), sodium bicarbonate (3.7 g/L, Sigma), L-glutamine (2 mM, Sigma), antibiotic-antimycotic solution (10 ml/L, Gibco), and calf serum (CS 10%, Integren). The vessels were perfused with the same media with the addition of Dextran (5% by weight, MW 282,000 Sigma). The test and control specimen both were maintained at body temperature and subjected to pulsatile flow in the physiological range. The control specimen was restored to and maintained at the in-vivo length, which corresponds to a stretch ratio of 1.5, for the duration of the experiment. The test specimen was stretched an additional 30% to a stretch ratio of 1.8 over the first two and one-half days of the five day experiment.

Bromodeoxyuridine ("BRDU") staining was used to compare the number of cells that were dividing in the test and control specimens. On the fifth day, the specimens were pressure-fixed with formalin and histologic slides prepared for cell counting using light microscopy. The BRDU was added on day four and the test specimen showed that 6.8+/−2.8% of the cells were dividing, while only 3.08+/−2.9% of the cells were dividing in the control specimen. The results clearly suggest that axial stretching can be used to enhance cell division in blood vessels, and should therefore be useful in the growing vessel segments for use in creating blood vessel grafts.

Modifications and variations of the present invention will be obvious to those of skill in the art from the foregoing detailed description. Such modifications and variations are intended to come within the scope of the following claims.

We claim:

1. An apparatus for growing a donor blood vessel of a human or animal in vitro comprising:
    a chamber containing a tissue culture medium;
    an inlet cannula;
    an outlet cannula; and
    a means for moving the inlet cannula, the outlet cannula, or both, to axially stretch an excised donor blood vessel secured between the inlet cannula and the outlet cannula in a submerged position in the tissue culture medium, wherein the inlet cannula, the outlet cannula, and the donor blood vessel can be secured together to form a conduit through which the tissue culture medium can flow,
    wherein the apparatus is operable to grow the donor blood vessel to increase its length.

2. The apparatus of claim 1, wherein the inlet cannula extends through a first orifice in the chamber, the inlet cannula having a first end outside of the chamber and a second end positioned inside the chamber, wherein the outlet cannula extends through a second orifice in the chamber, the outlet cannula having a first end outside of the chamber and a second end positioned inside the chamber, and wherein the donor blood vessel is securable by having a first end of the vessel secured to the second end of the inlet cannula and a second end of the vessel secured to the second end of the outlet cannula, thereby forming a conduit through the blood vessel and between the first end of the inlet cannula and the first end of the outlet cannula.

3. The apparatus of claim 1, wherein the chamber further comprises one or more apertures for gas exchange with the tissue culture medium.

4. The apparatus of claim 1, further comprising tissue culture medium flowing through the conduit.

5. The apparatus of claim 1, wherein the means for moving either or both of the cannula comprises a controller for moving the cannula in a continuous or intermittent manner.

6. The apparatus of claim 1, wherein the means for moving either or both of the cannula comprises a primer mover that is mechanically, electromechanically, or hydraulically driven.

7. The apparatus of claim 1, wherein either the inlet cannula or the outlet cannula is in a fixed position in the chamber, and the other cannula is moveable in a linear direction.

8. A method of forming a vascular graft in vitro for a human or animal in need thereof, comprising:
    securing one end of a donor blood vessel onto an end of an inlet cannula and securing the other end of the donor blood vessel onto an end of an outlet cannula, to form a conduit extending through the inlet cannula, the donor blood vessel, and the outlet cannula;
    submerging the donor blood vessel in tissue culture medium; and
    moving the inlet cannula, the outlet cannula, or both, axially to stretch and grow the donor blood vessel between the first end of the inlet cannula and the first end of the outlet cannula, forming a length of blood vessel suitable as a vascular graft.

9. The method of claim 8, further comprising flowing a tissue culture medium through the conduit.

10. The method of claim 9, wherein the donor blood vessel is maintained at body temperature and subjected to pulsatile flow of tissue culture medium in a physiological range.

11. The method of claim 8, wherein the donor blood vessel is selected from the group consisting of an internal mammary artery, a femoral artery, a gastroepipolic artery, a gastric artery, a radial artery, and a splenic artery.

12. The method of claim 8, wherein either or both of the cannula are moved continuously.

13. The method of claim 8, wherein either or both of the cannula are moved intermittently.

14. The method of claim 8, wherein the donor blood vessel is submerged in tissue culture medium provided in a chamber comprising one or more apertures for gas exchange with the tissue culture medium.

15. The method of claim 14, wherein the inlet cannula extends through a first orifice in the chamber, the inlet cannula having a first end outside of the chamber and a second end positioned inside the chamber, wherein the outlet cannula extends through a second orifice in the chamber, the outlet cannula having a first end outside of the chamber and a second end positioned inside the chamber, and wherein one end of the donor blood vessel is secured to the second end of the inlet cannula and the other end of the donor blood vessel is secured to the second end of the outlet cannula, thereby forming a conduit through the blood vessel and between the first end of the inlet cannula and the first end of the outlet cannula.

16. The method of claim 8, wherein the tissue culture medium comprises a growth factor and an antibiotic agent.

17. The method of claim 8, wherein the donor blood vessel is from a transgenic animals.

18. The method of claim 8, wherein the donor blood vessel is a genetically engineered tissue.

19. The method of claim 8, wherein the donor blood vessel is a vein from a human.

20. An apparatus for extending a donor blood vessel of a human or animal in vitro comprising:
   a chamber containing a tissue culture medium;
   an inlet cannula;
   an outlet cannula; and
   a primer mover operably connected to the inlet cannula, the outlet cannula, or both, to axially stretch an excised donor blood vessel secured between the inlet cannula and the outlet cannula in a submerged position in the tissue culture medium.

21. The apparatus of claim 1, wherein the tissue culture medium comprises a growth factor or other growth stimulating agent to enhance blood vessel growth.

22. The method of claim 8, wherein the stretched and grown blood vessel has a length greater than 30% of the donor blood vessel.

* * * * *